(12) United States Patent
Peterson

(10) Patent No.: US 9,784,313 B1
(45) Date of Patent: Oct. 10, 2017

(54) METHODS FOR SCREENING PCD ELEMENTS FOR EDM PROCESSING AND METHODS FOR EDM PROCESSING SUCH PCD ELEMENTS

(71) Applicant: US SYNTHETIC CORPORATION, Orem, UT (US)

(72) Inventor: S. Barrett Peterson, Orem, UT (US)

(73) Assignee: U.S. Synthetic Corporation, Orem, UT (US)

( * ) Notice: Subject to any disclaimer, the term of this patent is extended or adjusted under 35 U.S.C. 154(b) by 0 days.

(21) Appl. No.: 14/962,718

(22) Filed: Dec. 8, 2015

Related U.S. Application Data

(63) Continuation of application No. 14/455,154, filed on Aug. 8, 2014, now Pat. No. 9,239,307, which is a continuation of application No. 13/192,646, filed on Jul. 28, 2011, now Pat. No. 8,833,635.

(51) Int. Cl.
  *B23K 31/02* (2006.01)
  *F16C 33/04* (2006.01)
  *B23K 1/00* (2006.01)
  *B23K 31/10* (2006.01)
  *B23K 101/00* (2006.01)

(52) U.S. Cl.
  CPC .......... *F16C 33/043* (2013.01); *B23K 1/0008* (2013.01); *B23K 31/10* (2013.01); *B23K 2201/002* (2013.01)

(58) Field of Classification Search
  None
  See application file for complete search history.

(56) References Cited

U.S. PATENT DOCUMENTS

| | | |
|---|---|---|
| 3,949,062 A | 4/1976 | Vereschagin et al. |
| 4,268,276 A | 5/1981 | Bovenkerk |
| 4,410,054 A | 10/1983 | Nagel et al. |
| 4,468,138 A | 8/1984 | Nagel |
| 4,527,998 A | 7/1985 | Knemeyer |
| 4,560,014 A | 12/1985 | Geczy |
| 4,738,322 A | 4/1988 | Hall et al. |
| 4,811,801 A | 3/1989 | Salesky et al. |
| 4,913,247 A | 4/1990 | Jones |
| 5,001,452 A | 3/1991 | Imai et al. |
| 5,016,718 A | 5/1991 | Tandberg |
| 5,092,687 A | 3/1992 | Hall |
| 5,120,327 A | 6/1992 | Dennis |

(Continued)

FOREIGN PATENT DOCUMENTS

JP 2006-131439 5/2006

OTHER PUBLICATIONS

U.S. Appl. No. 12/830,878, filed Jul. 6, 2010, Wiggins, et al.

(Continued)

*Primary Examiner* — Kiley Stoner
(74) *Attorney, Agent, or Firm* — Holland & Hart

(57) ABSTRACT

Methods of screening a polycrystalline diamond element for suitability for electrical discharge machining ("EDM"). The method includes providing a PCD element including a plurality of bonded diamond grains, determining at least one characteristic of the PCD table correlated to electrical conductivity of the PCD element, and EDM the PCD element if the value of the at least one characteristic correlates to an electrical conductivity above a threshold value.

20 Claims, 12 Drawing Sheets

(56) References Cited

U.S. PATENT DOCUMENTS

| | | | |
|---|---|---|---|
| 5,135,061 A | 8/1992 | Newton, Jr. | |
| 5,154,245 A | 10/1992 | Waldenstrom et al. | |
| 5,364,192 A | 11/1994 | Damm et al. | |
| 5,368,398 A | 11/1994 | Damm et al. | |
| 5,460,233 A | 10/1995 | Meany et al. | |
| 5,480,233 A | 1/1996 | Cunningham | |
| 5,544,713 A | 8/1996 | Dennis | |
| 5,588,429 A | 12/1996 | Isaacson et al. | |
| 6,265,884 B1 | 7/2001 | Menashi et al. | |
| 6,270,898 B1 | 8/2001 | Yamamoto et al. | |
| 6,655,845 B1* | 12/2003 | Pope | A61F 2/30767 |
| | | | 384/491 |
| 6,793,681 B1 | 9/2004 | Pope et al. | |
| 7,552,782 B1 | 6/2009 | Sexton et al. | |
| 7,559,695 B2 | 7/2009 | Sexton et al. | |
| 7,866,418 B2 | 1/2011 | Bertagnolli et al. | |
| 7,870,913 B1* | 1/2011 | Sexton | F16C 33/043 |
| | | | 175/104 |
| 8,130,117 B2 | 3/2012 | Hall et al. | |
| 8,545,103 B1* | 10/2013 | Cooley | F16C 17/03 |
| | | | 384/306 |
| 8,833,635 B1 | 9/2014 | Peterson | |
| 9,037,430 B1* | 5/2015 | Wiggins | G06F 19/00 |
| | | | 702/45 |
| 2003/0019106 A1* | 1/2003 | Pope | A61L 27/04 |
| | | | 29/898 |
| 2004/0172885 A1 | 9/2004 | Middlemiss | |
| 2006/0144702 A1 | 7/2006 | Seki et al. | |
| 2006/0210364 A1* | 9/2006 | Bellmann | B23C 5/109 |
| | | | 407/40 |
| 2010/0218995 A1* | 9/2010 | Sexton | E21B 4/003 |
| | | | 175/57 |
| 2010/0300764 A1 | 12/2010 | Naidoo et al. | |
| 2011/0174544 A1* | 7/2011 | Scott | E21B 4/003 |
| | | | 175/92 |
| 2012/0241226 A1 | 9/2012 | Bertagnolli et al. | |
| 2013/0153778 A1 | 6/2013 | Sakoda et al. | |

OTHER PUBLICATIONS

U.S. Appl. No. 12/961,787, filed Dec. 7, 2010, Mukhopadhyay, et al.

Madaah-Hosseini et al.; A correlation between intrinsic coercivity-electrical conductivity-thermal treatment in a Nd11.9MM2.9Fe73.9Co3.3Ni1.1B6.9-type magnet; Journal of Alloys and Compounds 314 (2001); pp. 251-256.

U.S. Appl. No. 13/192,646, Nov. 14, 2013, Office Action.
U.S. Appl. No. 13/192,646, Feb. 27, 2014, Office Action.
U.S. Appl. No. 13/192,646, May 7, 2014, Notice of Allowance.
U.S. Appl. No. 13/192,646, Aug. 27, 2014, Issue Notification.
U.S. Appl. No. 14/455,154, May 4, 2015, Office Action.
U.S. Appl. No. 14/455,154, Sep. 4, 2015, Notice of Allowance.

* cited by examiner

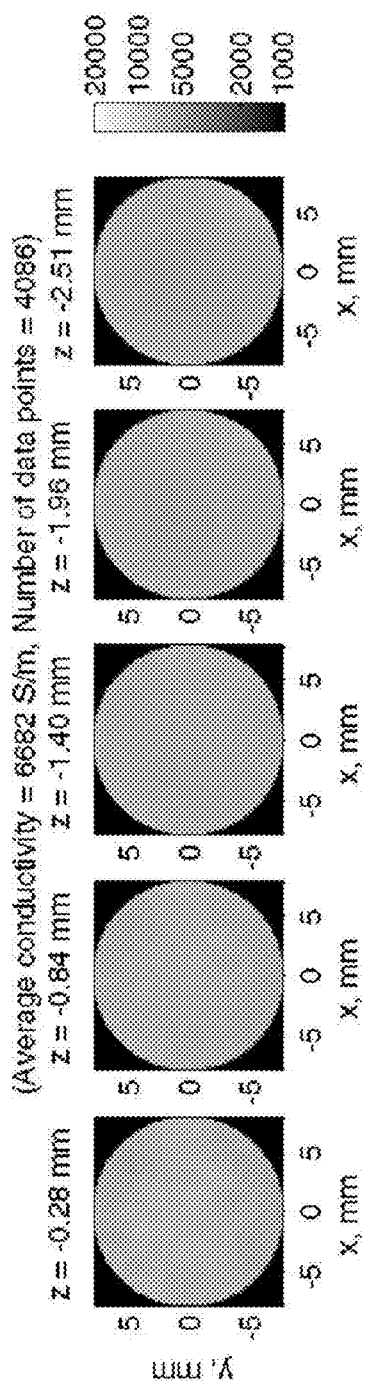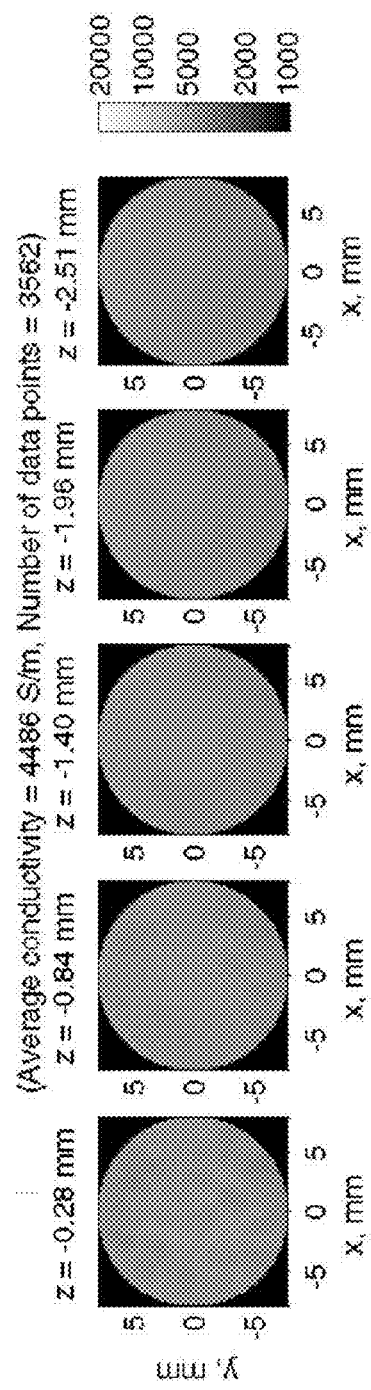
Fig. 6A
Fig. 6B

METHODS FOR SCREENING PCD ELEMENTS FOR EDM PROCESSING AND METHODS FOR EDM PROCESSING SUCH PCD ELEMENTS

CROSS-REFERENCE TO RELATED APPLICATIONS

This application is a continuation of U.S. application Ser. No. 14/455,154 filed on 8 Aug. 2014, which is a continuation of U.S. application Ser. No. 13/192,646 filed on 28 Jul. 2011 (now U.S. Pat. No. 8,833,635 issued on 16 Sep. 2014). The disclosure of each of the foregoing applications is incorporated herein, in its entirety, by this reference.

BACKGROUND

Wear-resistant, polycrystalline diamond compacts ("PDCs") are utilized in a variety of mechanical applications. For example, PDCs are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller-cone drill bits and fixed-cutter drill bits. A PDC cutting element typically includes a superabrasive diamond layer commonly known as a diamond table. The diamond table is formed and bonded to a substrate using a high-pressure/high-temperature ("HPHT") process. The PDC cutting element may be brazed directly into a preformed pocket, socket, or other receptacle formed in a bit body. The substrate may often be brazed or otherwise joined to an attachment member, such as a cylindrical backing. A rotary drill bit typically includes a number of PDC cutting elements affixed to the bit body. It is also known that a stud carrying the PDC may be used as a PDC cutting element when mounted to a bit body of a rotary drill bit by press-fitting, brazing, or otherwise securing the stud into a receptacle formed in the bit body.

Conventional PDCs are normally fabricated by placing a cemented carbide substrate into a container or cartridge with a volume of diamond particles positioned on a surface of the cemented carbide substrate. A number of such cartridges may be loaded into an HPHT press. The substrate(s) and volume(s) of diamond particles are then processed under HPHT conditions in the presence of a catalyst material that causes the diamond particles to bond to one another to form a matrix of bonded diamond grains defining a polycrystalline diamond ("PCD") table. The catalyst material is often a metal-solvent catalyst (e.g., cobalt, nickel, iron, or alloys thereof) that is used for promoting intergrowth of the diamond particles.

In one conventional approach, a constituent of the cemented carbide substrate, such as cobalt from a cobalt-cemented tungsten carbide substrate, liquefies and sweeps from a region adjacent to the volume of diamond particles into interstitial regions between the diamond particles during the HPHT process. The cobalt acts as a catalyst to promote intergrowth between the diamond particles, which results in formation of a matrix of bonded diamond grains having diamond-to-diamond bonding therebetween, with interstitial regions between the bonded diamond grains being occupied by the solvent catalyst. Once the PCD table is formed, the solvent catalyst may be at least partially removed from the PCD table of the PDC by acid leaching.

The performance of PDCs has been improving over the years as manufacturing technology advances. However, there can be some variability in characteristics within the PDC and PCD table that can depend on many input variables (e.g., temperature and pressures applied during HPHT processing, characteristics of the diamond feed, etc.). Without tracking such variables and the product produced with such variables, it can be difficult to differentiate between products produced under differing conditions. Such differing product may not be readily differentiated by simple visual inspection, and the differing characteristics of such products may interfere with the ability to further process such products in various ways.

SUMMARY

Embodiments of the invention relate to methods of screening PCD elements (e.g., PDCs and PCD tables) for suitability for electrical discharge machining ("EDM"). For example, EDM relies on the electrical conductivity of the material being EDM processed. Some PCD manufactured product may exhibit relatively low electrical conductivity as a result of low and/or isolated metal-solvent catalyst concentration within the PCD matrix (e.g., as a result of post HPHT process leaching, low metal-solvent catalyst concentration associated with higher pressure HPHT processing conditions, or other factors). The suitability of a particular PCD element for EDM processing generally cannot be readily determined by visual inspection. Thus, embodiments of the present invention provide a method by which suitability may be determined without having to actually attempt EDM of the PCD element.

According to an embodiment of a method, a PCD element is provided that includes a PCD table including a plurality of bonded diamond grains. At least one characteristic of the PCD table that is correlated to an electrical conductivity (e.g., electrical conductivity itself, electrical resistance, or another correlated characteristic) of the PCD table is determined, and if the value of the determined at least one characteristic correlates to an electrical conductivity above a threshold value, then the PCD table is EDM processed.

Embodiments of the present invention enable EDM of suitable product to occur, which is often less expensive and faster than alternative cutting or machining methods (e.g., lapping, grinding, laser cutting, etc.) that can be used as an alternative when EDM is not practical because the electrical conductivity of the PCD table to be cut is too low.

Such methods may be particularly advantageous in the fabrication of bearing assemblies in which a plurality of PDCs are typically brazed onto the bearing assembly. While bearings may sometimes be pre-cut (i.e., prior to brazing onto the bearing assembly), there is typically a final EDM operation performed after brazing. When EDM is not possible and/or practical because one of the PCD elements has unsuitable electrical characteristics, the entire bearing assembly may have to be scrapped, which can be very expensive. Thus, according to an embodiment for fabricating a bearing assembly, a bearing element including a PCD element including a plurality of bonded diamond grains is provided, at least one characteristic of the PCD element that is correlated to electrical conductivity (e.g., electrical conductivity itself, electrical resistance, or another characteristic correlated to electrical conductivity) of the PCD element is determined, and if the determined at least one characteristic correlates to an electrical conductivity above a threshold value, then the PCD element is brazed onto a bearing assembly. Brazing of the PCD element only occurs after the correlated at least one characteristic has been determined and the PCD table has been found suitable for EDM. This prevents a PCD element that cannot be EDM processed, as a practical matter, from being brazed onto a bearing assembly, which may then have to be scrapped.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

FIGS. 6A and 6B are electrical conductivity distributions in PCD tables of two different PDC cutter samples, with the electrical conductivity grey scale in Siemens/meter ("S/m");

DETAILED DESCRIPTION

I. Introduction

Figure 1:
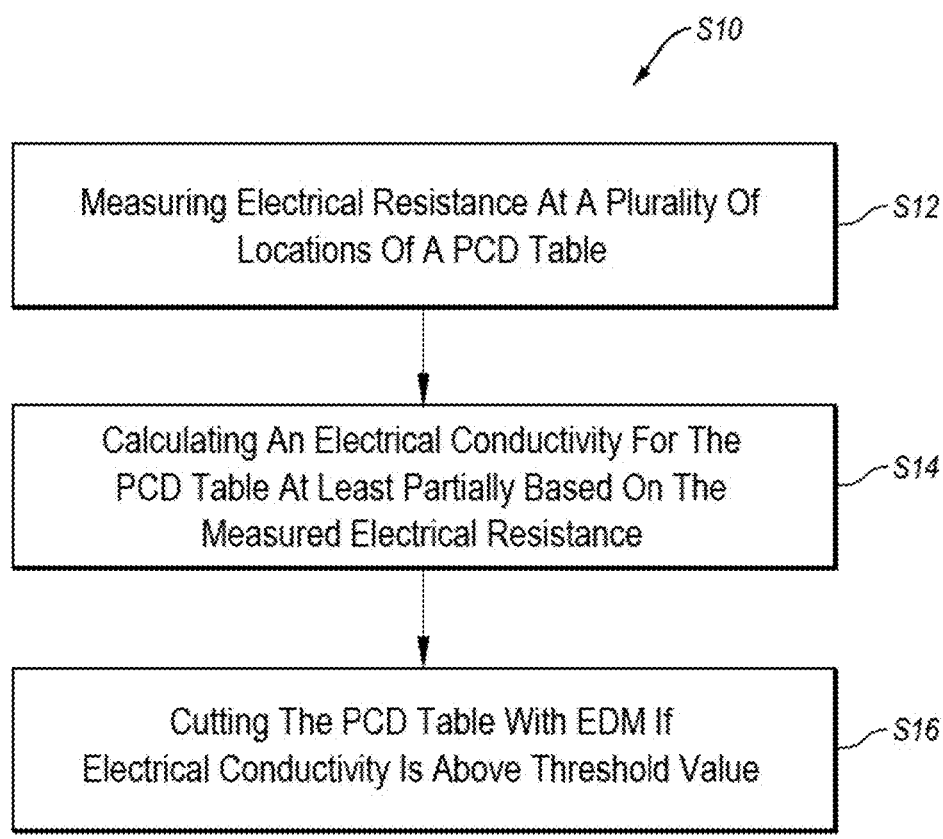
FIG. 1 is a flow diagram for screening and qualifying a PCD element for an EDM process according to an embodiment.

Embodiments of the present invention are directed to methods of screening a PCD element for suitability for EDM. According to an embodiment, the method includes providing a PCD element (e.g., a PDC, a PCD table, or other type of PCD body) comprising a plurality of bonded diamond grains, determining at least one characteristic of the PCD element correlated to the electrical conductivity of the PCD element, and EDM the PCD element if a value of the determined at least one characteristic correlates to an electrical conductivity above a threshold value.

The methods may be employed for screening PCD product manufactured under different conditions, which have become intermingled together and which are not readily differentiable from one another based on simple inspection procedures (e.g., visual inspection). For example, some of the PCD product may have been formed under exceptionally high pressure conditions (e.g., at least about 7.5 GPa cell pressure), which may result in a relatively lower concentration of metal-solvent catalyst interspersed interstitially between the diamond grains. In an embodiment, the metal-solvent catalyst concentration is about 7.5% by weight or less (e.g., about 0% to about 7.5% by weight). Decreasing metal-solvent catalyst concentration has been found to correlate with decreasing electrical conductivity.

The methods may be employed in fabrication of a bearing assembly from screened polycrystalline diamond elements. Such a method may include providing a bearing element comprising a PCD element including a plurality of bonded diamond grains, determining one or more characteristics of the PCD element correlated to electrical conductivity of the PCD element, EDM the PCD element if the value of the determined correlated characteristic correlates to an electrical conductivity above a threshold value, and brazing the bearing element onto a supporting ring after it has been determined that the electrical conductivity is above the threshold value. Such methods prevent PCD elements that are unsuitable for EDM from being brazed onto the bearing assembly, which can result in the assembly having to be scrapped as down-line EDM processing may not be possible.

II. Embodiments of PCD Elements

The PCD elements capable of being screened using the methods disclosed herein include PCD tables of one-step and two-step PDCs and freestanding PCD tables/elements. A one-step PDC may include a PCD table integrally formed and bonded to a cemented carbide substrate. The PCD table includes directly bonded-together diamond grains exhibiting diamond-to-diamond bonding (e.g., $sp^3$ bonding) therebetween that define a plurality of interstitial regions. An embodiment of a PDC 200 including a PCD table 202 and a cemented carbide substrate 204 is shown as part of FIG. 2. The PCD table 202 includes at least one lateral surface 205, an upper exterior working surface 203, and may include an optional chamfer 207 formed therebetween. It is noted that at least a portion of the at least one lateral surface 205 and/or the chamfer 207 may also function as a working surface (e.g., that contacts a subterranean formation during drilling operations).

A metal-solvent catalyst (e.g., iron, nickel, cobalt, or alloys thereof) is disposed in at least a portion of the interstitial regions between adjacent diamond grains. The cemented carbide substrate 204 may comprise tungsten carbide, tantalum carbide, vanadium carbide, niobium carbide, chromium carbide, titanium carbide, or combinations of the foregoing carbides cemented with iron, nickel, cobalt, or alloys of the foregoing metals. For example, the cemented carbide substrate may comprise cobalt-cemented tungsten carbide.

Generally, a one-step PDC may be formed by placing un-bonded diamond particles adjacent to a cemented carbide substrate and subjecting the diamond particles and the cemented carbide substrate to an HPHT process under diamond-stable HPHT conditions. During the HPHT process, metal-solvent catalyst from the cemented carbide substrate at least partially melts and sweeps into interstitial regions between the diamond particles to catalyze growth of diamond and formation of diamond-to-diamond bonding between adjacent diamond particles so that a PCD table is formed that bonds to the cemented carbide substrate upon cooling from the HPHT process.

A two-step PDC may also be formed in which an at least partially leached PCD table (i.e., a freestanding PCD table) may be placed adjacent to a cemented carbide substrate and subjected to an HPHT process under diamond-stable conditions. During the HPHT process, an infiltrant from the cemented carbide substrate or other source infiltrates into the interstitial regions of the at least partially leached PCD table and bonds the infiltrated PCD table to the cemented carbide substrate upon cooling from the HPHT process. Additional details of an exemplary two-step process for forming a PDC are disclosed in U.S. patent application Ser. No. 12/961,787 filed Dec. 7, 2010 and herein incorporated by reference in its entirety.

The at least partially leached PCD table may be formed by separating the PCD table from a one-step PDC by removing the cemented carbide substrate via any suitable process (e.g., grinding, machining, laser cutting, EDM, or combinations thereof) and leaching the metal-solvent catalyst from the PCD table in a suitable acid. The at least partially leached PCD table may also be formed by other methods, such as sintering diamond particles in the presence of a metal-solvent catalyst to form a PCD table or disk and leaching the PCD table in a suitable acid.

Both one-step and two-step PDCs may be subjected to a leaching process to remove a portion of the metal-solvent catalyst or infiltrant from the PCD table to a selected depth and from one or more exterior surfaces. Removal of the metal-solvent catalyst or infiltrant may help improve thermal stability and/or wear resistance of the PCD table during use.

Exemplary acids used in leaching include, but are not limited to, aqua regia, nitric acid, hydrofluoric acid, and mixtures thereof. For example, leaching the PCD table 202 may form a leached region that extends inwardly from the exterior surface 203, the lateral surface 205, and the chamfer 207 to a selected leached depth. The selected leached depth may be about 100 µm to about 1000 µm, about 100 µm to about 300 µm, about 300 µm to about 425 µm, about 350 µm to about 400 µm, about 350 µm to about 375 µm, about 375 µm to about 400 µm, about 500 µm to about 650 µm, or about 650 µm to about 800 µm.

The bonded together diamond grains of the PCD table may exhibit an average grain size of about 100 µm or less, about 40 µm or less, such as about 30 µm or less, about 25 µm or less, or about 20 µm or less. For example, the average grain size of the diamond grains may be about 10 µm to about 18 µm, about 8 µm to about 15 µm, about 9 µm to about 12 µm, or about 15 µm to about 25 µm. In some embodiments, the average grain size of the diamond grains may be about 10 µm or less, such as about 2 µm to about 5 µm or submicron.

The diamond particle size distribution of the diamond particles that are HPHT processed may exhibit a single mode, or may be a bimodal or greater grain size distribution. In an embodiment, the diamond particles may comprise a relatively larger size and at least one relatively smaller size. As used herein, the phrases "relatively larger" and "relatively smaller" refer to particle sizes (by any suitable method) that differ by at least a factor of two (e.g., 30 µm and 15 µm). According to various embodiments, the diamond particles may include a portion exhibiting a relatively larger average particle size (e.g., 50 µm, 40 µm, 30 µm, 20 µm, 15 µm, 12 µm, 10 µm, 8 µm) and another portion exhibiting at least one relatively smaller average particle size (e.g., 6 µm, 5 µm, 4 µm, 3 µm, 2 µm, 1 µm, 0.5 µm, less than 0.5 µm, 0.1 µm, less than 0.1 µm). In an embodiment, the diamond particles may include a portion exhibiting a relatively larger average particle size between about 10 µm and about 40 µm and another portion exhibiting a relatively smaller average particle size between about 1 µm and 4 µm. In some embodiments, the diamond particles may comprise three or more different average particle sizes (e.g., one relatively larger average particle size and two or more relatively smaller average particle sizes), without limitation.

It is noted that the as-sintered diamond grain size may differ from the average particle size of the diamond particles prior to sintering due to a variety of different physical processes, such as grain growth, diamond particles fracturing, carbon provided from another carbon source (e.g., dissolved carbon in the metal-solvent catalyst), or combinations of the foregoing.

The PCD table 202 may exhibit a thickness "t" of at least about 0.040 inch, such as about 0.045 inch to about 1 inch, about 0.045 inch to about 0.500 inch, about 0.050 inch to about 0.200 inch, about 0.065 inch to about 0.100 inch, or about 0.070 inch to about 0.100 inch (e.g., about 0.09 inch).

U.S. Pat. No. 7,866,418, herein incorporated by reference, discloses PCD tables and associated PDCs formed under conditions in which enhanced diamond-to-diamond bonding occurs. Such enhanced diamond-to-diamond bonding is believed to occur as a result of the sintering pressure (e.g., at least about 7.5 GPa cell pressure) employed during the HPHT process being further into the diamond stable region, away from the graphite-diamond equilibrium line.

The PCD tables and PDCs disclosed in U.S. Pat. No. 7,866,418, as well as methods of fabrication, may be screened for EDM processing according to the methods disclosed herein. For example, generally, as the sintering pressure that is used to form the PCD increases, a coercivity of the PCD may increase and the magnetic saturation of the PCD may decrease. The PCD defined collectively by bonded diamond grains and metal-solvent catalyst may exhibit a coercivity of about 115 Oe or more and a metal-solvent catalyst content of less than about 7.5% by weight as indicated by a specific magnetic saturation of about 15 G·cm³/g or less. In a more detailed embodiment, the coercivity of the PCD may be about 115 Oe to about 250 Oe and the specific magnetic saturation of the PCD may be greater than zero G·cm³/g to about 15 G·cm³/g. In an even more detailed embodiment, the coercivity of the PCD may be about 115 Oe to about 175 Oe and the specific magnetic saturation of the PCD may be about 5 G·cm³/g to about 15 G·cm³/g. In yet an even more detailed embodiment, the coercivity of the PCD may be about 155 Oe to about 175 Oe and the specific magnetic saturation of the PCD may be about 10 G·cm³/g to about 15 G·cm³/g. The specific permeability (i.e., the ratio of specific magnetic saturation to coercivity) of the PCD may be about 0.10 or less, such as about 0.060 to about 0.090.

Despite the average grain size of the bonded diamond grains of the PCD being less than about 30 µm, the metal-solvent catalyst content in the PCD may be less than about 7.5% by weight resulting in a desirable thermal stability. In an embodiment, diamond particles having an average particle size of about 18 µm to about 20 µm are positioned adjacent to a cobalt-cemented tungsten carbide substrate and subjected to an HPHT process at a temperature of about 1390° C. to about 1430° C. and a cell pressure of about 7.8 GPa to about 8.5 GPa. The PCD so-formed as a PCD table bonded to the substrate may exhibit a coercivity of about 155 Oe to about 175 Oe, a specific magnetic saturation of about 10 G·cm³/g to about 15 G·cm³/g, and a cobalt content of about 5% by weight to about 7.5% by weight.

Besides enhanced diamond-to-diamond bonding, such PCD elements formed according to the methods of U.S. Pat. No. 7,866,418 may be characterized by relatively low metal-solvent catalyst or infiltrant concentrations (e.g., about 7.5% by weight or less). In some embodiments, the metal-solvent catalyst or infiltrant may be present in the PCD table in an amount of about 3% to about 7.5% by weight, about 3% to about 6% by weight, about 3% by weight or less, about 1% to about 3% by weight, or about 1% by weight.

As described above, the PCD table 202 may be formed separately from or integral with the substrate 204 in an HPHT process. When formed separately, the PCD table 202 may be subsequently attached to the substrate 204 in another HPHT process (i.e., the PCD is fabricated in a two-step process). The temperature of such HPHT processes may typically be at least about 1000° C. (e.g., about 1200° C. to about 1600° C.) and the pressure of the HPHT process may typically be at least about 4.0 GPa (e.g., about 5.0 GPa to about 12.0 GPa, about 7.0 GPa to about 9.0 GPa, about 6.0 GPa to about 8.0 GPa, or about 9.0 GPa to about 12.0 GPa).

Although diamond is not electrically conductive by itself, the sintering process for fabricating PCD introduces small amounts of metal-solvent catalyst (e.g., iron, nickel, cobalt, or alloys thereof) into the interstitial regions between the bonded diamond crystals of the PCD. For example, cobalt is molten during sintering of diamond crystals, and acts as a solvent catalyst that promotes diamond-to-diamond crystal bonding between the diamond crystals during the HPHT sintering process. The macroscopic electrical conductivity of PCD may be closely related to the metal-solvent catalyst content therein.

Additives to the PCD table may also influence the electrical conductivity thereof. For example, the PCD table may include silicon, silicon carbide, graphite, tungsten, tungsten carbide, boron, combinations thereof, or other selected constituents. Some additives may be alloyed with the metal-solvent catalyst of the PCD table that is present interstitially between bonded diamond crystals. For example, cobalt may be alloyed with tungsten and/or boron.

Once the PCD table has been formed, subsequent fabrication steps for machining or otherwise shaping and finishing the PCD table are often performed. One method of machining the PCD table and very hard substrate materials that has generally been cost effective is EDM, in which is a desired shape is obtained using electrical discharge machining. Material may be removed from the PCD table as a result of electrical discharge between a tool electrode and the PCD table, as will be known to those of skill in the art. The tool electrode may be a wire (e.g., wire EDM), a so-called "plunge" electrode, or any other known EDM electrode.

EDM processing relies on the workpiece (e.g., the PCD table) being sufficiently electrically conductive to support the EDM process by which the electrical discharge flows from the EDM wire or other EDM tool to the workpiece, resulting in controlled removal of material. The metal solvent catalyst or other infiltrant that is interstitially disposed within the PCD table between diamond grains can provide the needed electrical conductivity, although where the PCD has been leached, insufficient electrically conductive catalyst or infiltrant may be present to support EDM as a practical matter. In other words, while it may be possible to EDM a PCD table including a relatively low solvent catalyst/infiltrant concentration, this may not be practical as the EDM may take significantly longer than an acceptable period of time (e.g., about 5 minutes or less).

Other fabrication factors (e.g., ultra high pressure during HPHT processing) can also result in significantly lower interstitial metal-solvent catalyst/infiltrant concentration within the PCD table. Because PCD elements may be intermingled following fabrication but before any EDM, it may not be possible to differentiate one type of product (that may have sufficient catalyst/infiltrant concentration to support EDM processing) from another (which may not have sufficient catalyst/infiltrant concentration to support EDM processing). Embodiments of the present invention provide methods for quickly and efficiently screening qualifying PCD elements for suitability for EDM processing by determining electrical conductivity of the PCD table or a characteristic (e.g., electrical resistance) that correlates to electrical conductivity.

As used herein, the phrase "characteristic correlated to electrical conductivity" and related terms and phrases include electrical conductivity itself, as well as any other characteristic that may be measured and correlated to electrical conductivity. An example of such a characteristic is electrical resistance or electrical impedance.

III. Determining a Characteristic Correlated to Electrical Conductivity

FIG. 1 shows a flow diagram generally describing a method S10 for screening or qualifying a PCD element for an EDM process by measuring electrical resistance according to an embodiment. At S12 electrical resistance is measured at a plurality of locations of a PCD table. At S14, an average electrical conductivity for the PCD table is calculated based at least partially on the measured electrical resistance. Because measurements are taken at a plurality of locations, any non-uniformity within the distribution of the electrical conductivity of the PCD table may also be determined, if desired. The existence of such non-uniformities (e.g., regions of significantly higher or lower conductivity) can be due to poorly sintered diamond crystals, high metal-solvent catalyst content regions, porosity and/or cracks. The calculated electrical conductivity is compared to a threshold value, and at S16 the PCD table is cut using EDM if the determined electrical conductivity is above the threshold value.

It will be readily apparent to one of skill in the art that actual calculation of the electrical conductivity of the PCD table is not necessary, as one may alternatively compare the measured electrical resistance (or another characteristic that correlates to electrical conductivity) to a threshold value known to correlate to the threshold electrical conductivity value. In another embodiment, the electrical conductivity may be measured directly.

Figure 2:
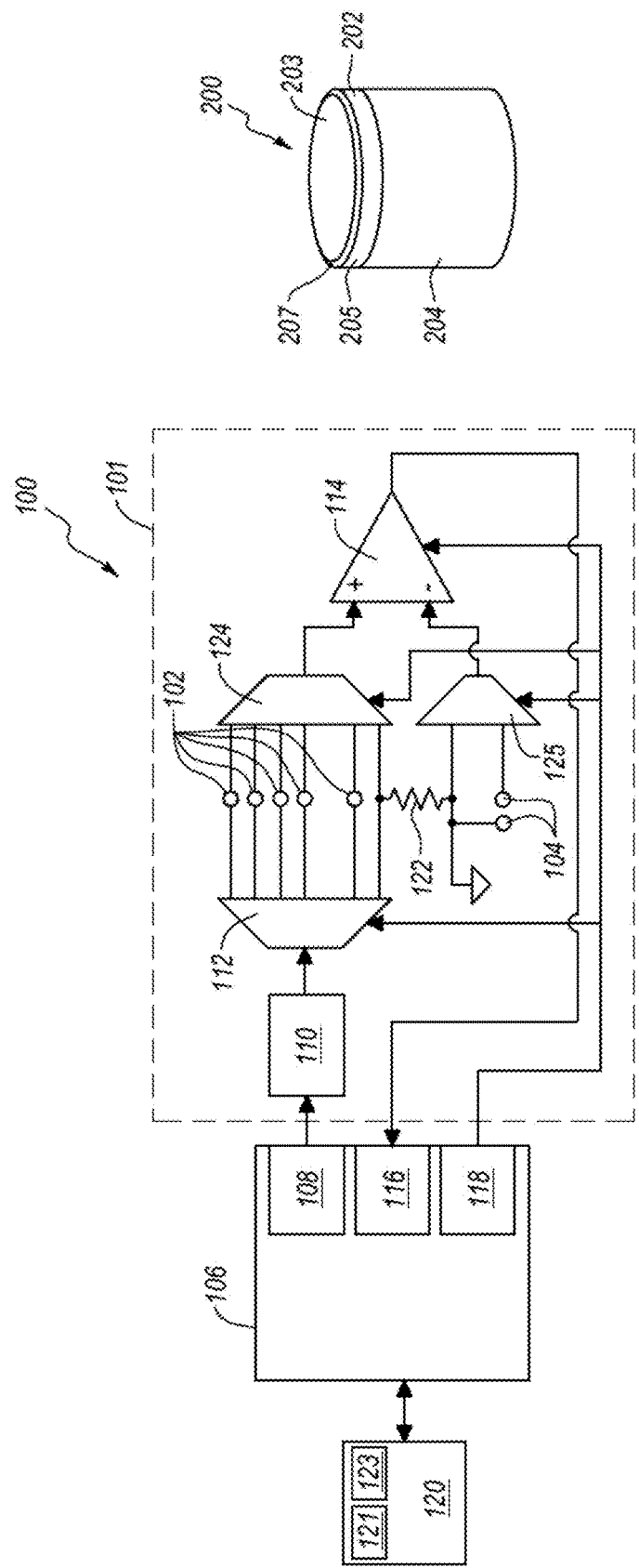
FIG. 2 is a functional block diagram of an embodiment of a multi-probe resistance measurement testing system configured to measure electrical resistance of a PCD table that may be used in the methods disclosed herein.

FIG. 2 is a functional block diagram of an embodiment of a multi-probe resistance measurement electrical impedance testing ("EIT") system 100 that may be used to measure electrical resistance or impedance. The system 100 includes an EIT unit 101 configured to measure an electrical resistance of the PCD 202 at a plurality of locations. The EIT unit 101 may include a plurality of probes 102 (e.g., 121 spring-loaded probes) configured to electrically contact a surface 203 of the PCD table 202 of the PDC 200, and a plurality of probes 104 (e.g., two probes) to contact the substrate 204 of the PDC sample 200. For example, the probes 102 may be spring-loaded pins (e.g., "pogo" pins used in printed circuit board testing) that make contact with the surface 203 of the PCD table 202. Resistance measurements may be acquired and recorded at a plurality of different locations when 121 of the probes 102 and the probes 104 are used in the system 100. The electrical resistance measurements may then be reconstructed into a 3D electrical conductivity distribution of the PCD table 202 using a reconstruction algorithm.

Figure 3:
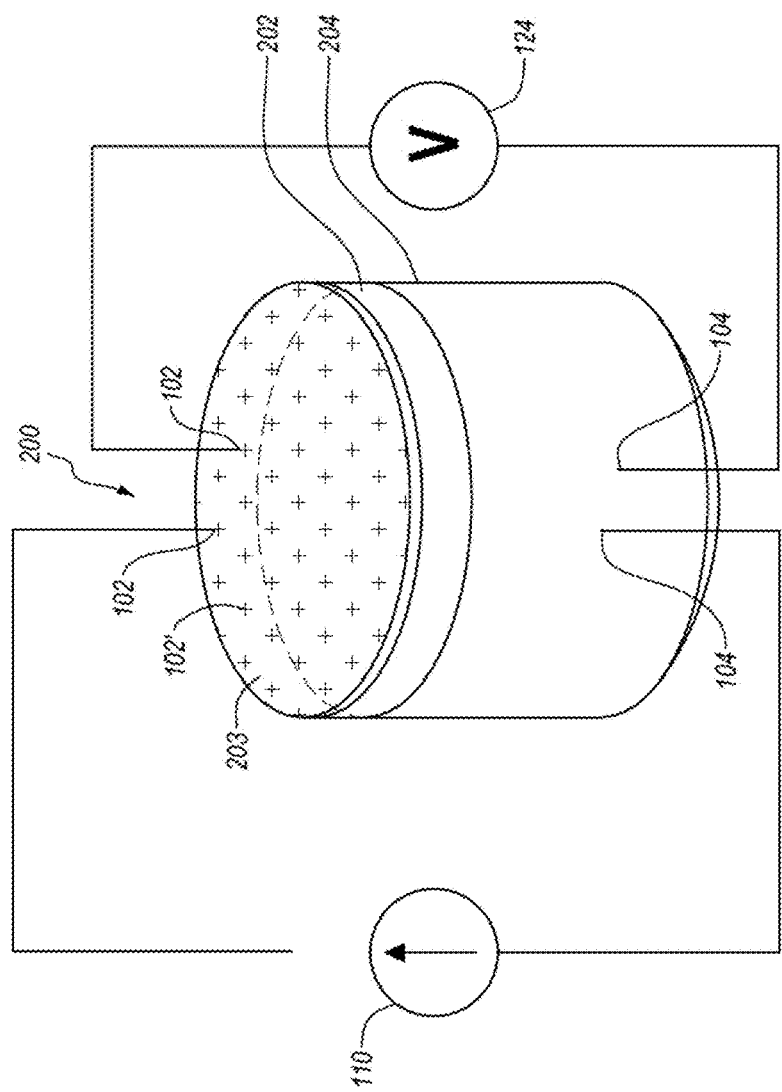
FIG. 3 is a schematic diagram for four-probe electrical resistance measurements on a PDC sample using the system shown in FIG. 2.

The system 100 may be configured to make 4-probe DC resistance measurements in the approximate range from 0.1 mΩ To 1Ω on the PDC sample 200. The substrate 204 of the PDC sample 200 may be used as a reference conductor. One of the current probes and one of the voltage probes may be electrically connected to the substrate 204. The 4-probe measurement setup may be completed by multiplexing one of the top surface-contacting probes 102 for current injection and another of the top surface-contacting probes 102 for voltage measurement. Probe locations for the probes 102 are shown in the schematic diagram of FIG. 3 as + shapes and only one location is labeled as 102' for sake of clarity. Using this probe arrangement, only one large current multiplexer and one large voltage multiplexer may be required.

Referring again to FIG. 2, the system 100 includes a data acquisition module 106 (e.g., a USB data acquisition) coupled to the EIT unit 101. The data acquisition module 106 includes an analog output 108 that controls the output current of a precision current source 110 in the range from about −150 mA to about +150 mA. The current is routed to one of the 121 sensor probes 102 in contact with the PCD table 202 through a 1:128 current multiplexer 112. For example, the current multiplexer 112 may be built using commercially available 8:1 analog multiplexers with 5Ω maximum series 'on' resistance. One of the reference probes 104 contacting the substrate 204 serves as a current sink and is grounded. A respective voltage measurement is taken between the sensor probe 102 selected by the 128:1 voltage multiplexer 124 and the second reference probe 104 contacting the substrate. The voltage is amplified by a programmable-gain instrumentation amplifier 114 and sent to an analog input 116 of the data acquisition module 106. The amplifier 114 may be programmed for gains of, for example, about 1, about 250, about 1000, and about 4000. Unity gain may be used for probe contact resistance measurement. A plurality of digital outputs 118 (e.g., 18 total) from the data acquisition module 106 control all the multiplexers and the amplifier gain of the amplifier 124.

A computer 120 (e.g., a desktop computer) is coupled to or includes the data acquisition module 106 therein. The computer 120 receives the electrical resistance measurements taken by the EIT unit 101 from the analog input 116 of the data acquisition module 106. The computer 120 includes memory 121 storing software thereon containing computer executable instructions configured for reconstructing/calculating/analyzing the electrical conductivity distribution in the PCD table 202 of the PDC sample 200 being tested in accordance with a reconstruction algorithm and one or more processors 123 for executing the computer executable instructions. For example, the one or more processors 123 may control the data acquisition module 106 and process the measured resistance data to reconstruct and analyze the electrical conductivity distribution.

To calibrate the instrument, one or more precision reference resistors 122 are provided, such as 50 mΩ, 20 mΩ and 10 mΩ in an embodiment. A secondary 4:1 voltage multiplexer 125 may be provided to accommodate 4-wire measurements of these reference resistors 122. FIG. 2 shows only one exemplary reference resistor, but the connections of the other reference resistors may be similar.

Figure 4:
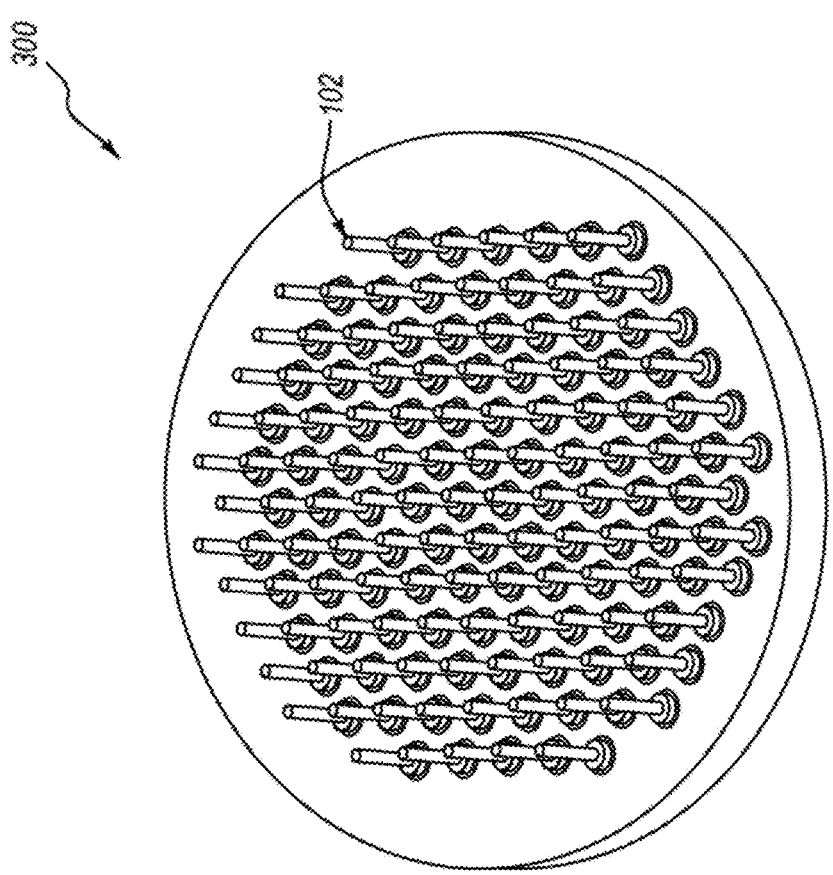
FIG. 4 is a top isometric view of the sensor-probe arrangement of the testing system shown in FIG. 3.

Referring to FIG. 4, an embodiment for a sensor assembly 300 of the EIT unit 101 including a plurality of probes 102 is illustrated. In an embodiment, the probes 102 may be arranged in a triangular-grid pattern. It should be noted that other sensor-assembly configurations may be used, e.g., for PDC samples having a different size and/or a different configuration.

Figure 5A:
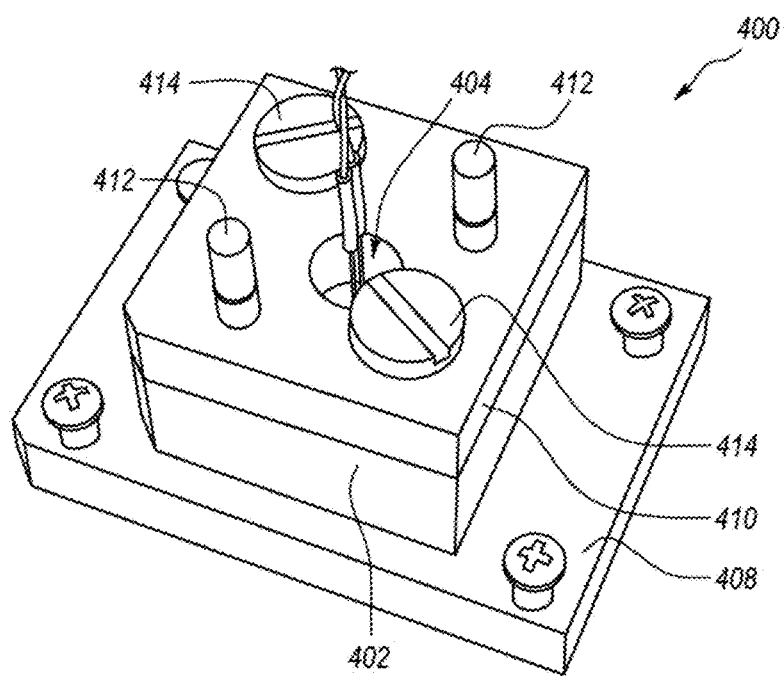
FIG. 5A is an isometric view of an embodiment of a sample-holder assembly for holding a PDC sample to be tested.
Figure 5B:
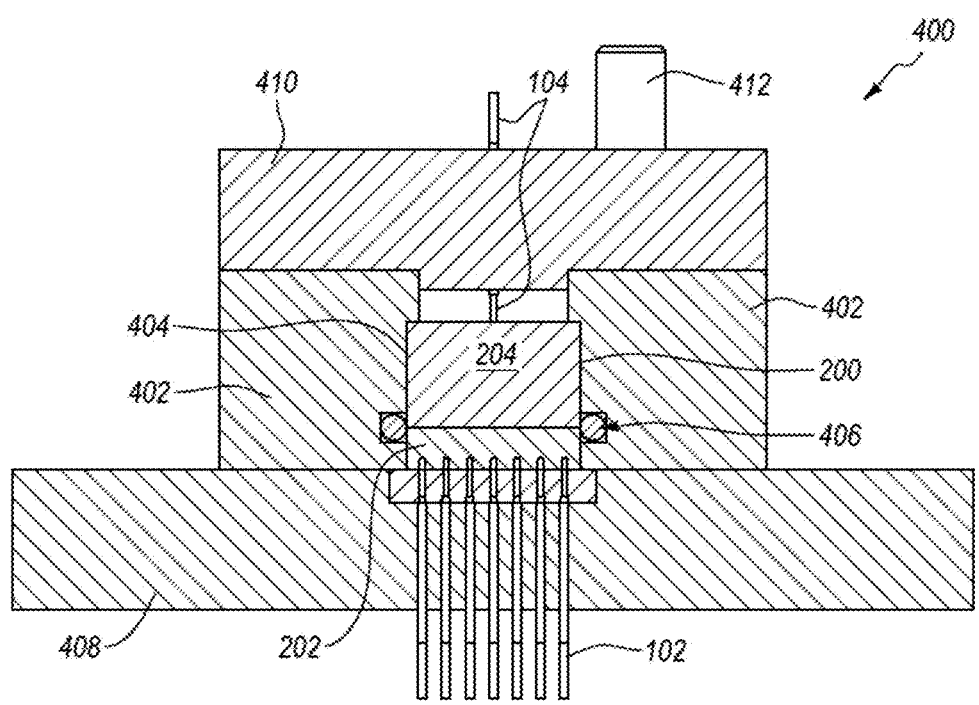
FIG. 5B is a cross-sectional view of the sample-holder assembly shown in FIG. 5A, with a PDC sample to be tested held therein.

FIGS. 5A and 5B illustrate an embodiment of a sample holder 400 that facilitates placement of the PDC sample 200 to be tested using the system 100 so that reliable electrical contact with the sensor probes 102 and 104 may be established. The main body 402 has a cavity 404 therein configured for holding the PDC sample 200. The PDC sample 200 may be centered and held in place by a resilient member 406 (e.g., a soft O-ring) that is disposed in a groove formed in the main body 402 that encircles the PDC sample 200 and defines part of the cavity 404. The resilient member 406 allows turning the part holder upside-down to place the part on top of the spring-loaded probes 102. The probes 102 are installed in and project outwardly from a base 408 having corresponding holes (e.g., 121 holes) drilled therein. The sensor assembly 400 may include a cap 410 that carries the reference probes 104 that contact the substrate 204 of the PDC sample 200. One or more dowel pins 412 or other alignment structure may extend through sample holder components 402, 408, and 410 to keep them in alignment. Referring specifically to FIG. 5A, the components of the sample holder 400 may be compressed together so that the probes 102 and 104 are in electrical contact with the PDC sample 200 by, for example, thumb screws 414 or other compression mechanism.

A conductive paste and/or coating (e.g., a conductive grease containing silver, copper, gold, or combinations thereof) may be applied to the surface 203 of the PCD table 202 to help reduce any occurrence of poor probe contact.

The described system 100 was used to test a variety of PDC samples. Each PDC sample included a cobalt-cemented carbide substrate having a PCD table bonded thereto. The PCD tables were comprised of a plurality of bonded-together diamond crystals having cobalt infiltrated from the substrate and disposed interstitially between the bonded-together diamond crystals. The electrical conductivity distributions of PCD tables from two PDCs having substantially homogenous PCD tables are shown in FIGS. 6A and 6B. Five slices through the 3D electrical conductivity distribution are shown at varying depths into the PCD table measured from an upper surface of the PCD table (e.g., the upper surface 203 in FIG. 2). The depth is indicated above each slice. Even though the electrical conductivity is substantially homogeneous, the average electrical conductivity varied from sample to sample, and was found to be strongly influenced by metal-solvent catalyst content.

Additional details of suitable EIT testing systems and additional results are disclosed in U.S. patent application Ser. No. 12/830,878 filed Jul. 6, 2010 and entitled METHODS FOR NON-DESTRUCTIVELY TESTING A POLYCRYSTALLINE DIAMOND ELEMENT, RELATED ELECTRICAL IMPEDANCE TOMOGRAPHY SYSTEMS, AND ROTARY DRILL BIT INCLUDING SELECTIVELY ORIENTED POLYCRYSTALLINE DIAMOND CUTTER, incorporated herein, in its entirety, by this reference. It should be noted that the described EIT testing system is only one suitable system for determining electrical conductivity. Other measurement systems and techniques may be employed.

IV. Embodiments of EDM Methods

Figure 7A:
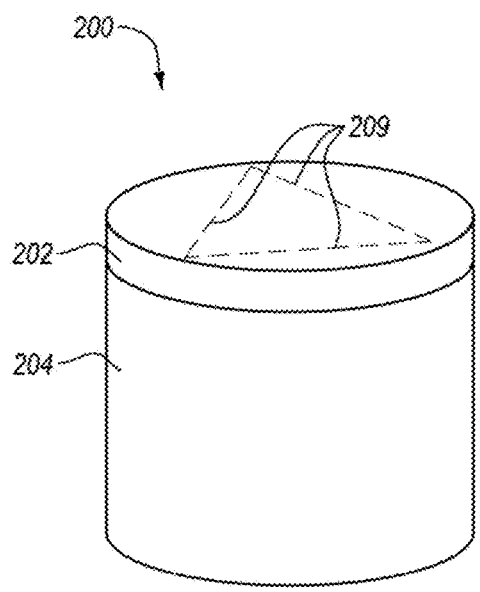
FIG. 7A is an isometric view of a PDC including an EDM cut formed into a PCD table according to an embodiment.
Figure 7B:
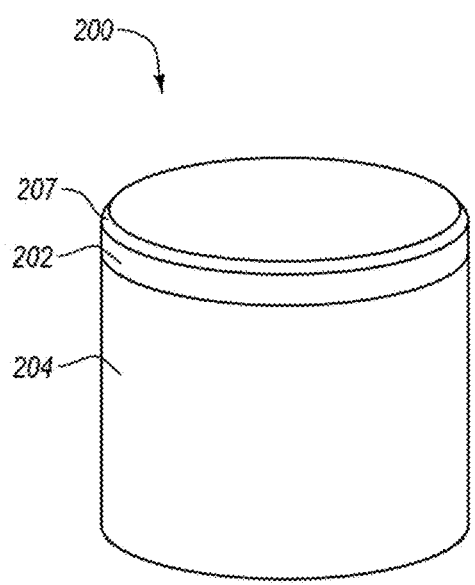
FIG. 7B is a isometric view of a PDC including an PCD table with a chamfer that may be formed by EDM according to an embodiment.
Figure 7C:
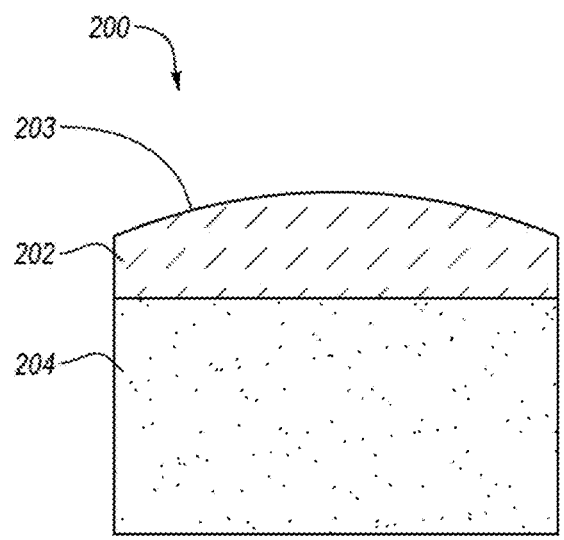
FIG. 7C is a cross-sectional view of a PDC including a PCD table for use in a radial bearing in which the convex curvature of the bearing surface of the PCD table has been formed by EDM according to an embodiment.

EDM processes may be used to cut and/or shape any of various features into a PCD table, a PDC, or other PCD element. EDM may also be used to cut or shape other portions of the PDC (e.g., the substrate 204). FIGS. 7A-7C illustrate non-limiting embodiments of features that may be cut, shaped, or otherwise formed into a PCD table. FIG. 7A shows a PDC 200 including a PCD table 202 bonded to a carbide substrate 204. One or more grooves 209 has been EDM cut (e.g., by wire or plunge EDM) into PCD table 202. Because the PCD table 202 was screened so that it was prequalified for EDM before any attempt to EDM the table 202, the EDM may proceed quickly, without any significant risk that EDM will not be possible because of insufficient electrical conductivity of the PCD table 202.

EDM formed grooves or cuts 209 may be formed into surface of PCD table 202 to form a triangular or other shaped PCD table. Although a particular geometry of EDM formed grooves or cuts is described, it will be understood that one or more EDM formed cuts or grooves may be formed anywhere within PCD table 202 (and optionally in carbide substrate 204) for any desired purpose (e.g., to provide a desired shape to PCD table 202, curve a bearing surface, etc.).

FIG. 7B illustrates formation of a chamfer 207 into the PCD table 202 of the PDC 200. Although such a chamfer 207 may be formed by other techniques (e.g., grinding) such a chamfer 207 may also be formed by EDM.

Figure 7D:
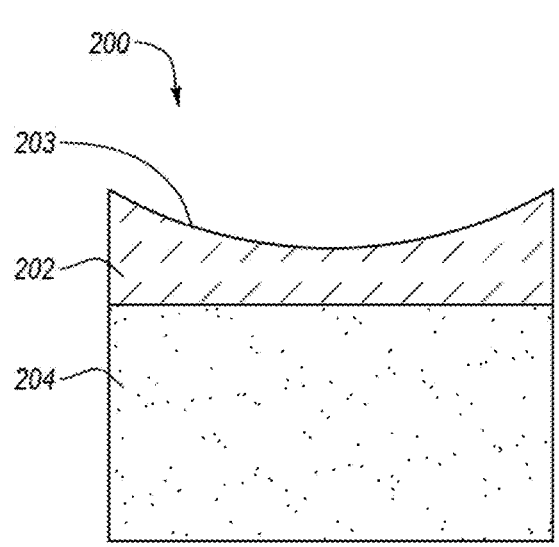
FIG. 7D is a cross-sectional view of a PDC including a PCD table for use in a radial bearing in which the concave curvature of the bearing surface of the PCD table has been formed by EDM according to an embodiment.

FIG. 7C illustrates a cross-sectional view through a PDC 200 including a PCD table 202 that has been EDM cut to include a convex curvature along working exterior top surface 203. FIG. 7D illustrates a cross-sectional view through a PDC 200 including a PCD table 202 that has been EDM cut to include a concave curvature along working exterior top surface 203. Such PDCs including a convexly and concavely shaped PCD tables 202 may be particularly useful in a radial bearing assembly as shown and further described in conjunction with FIG. 12.

Figure 8:
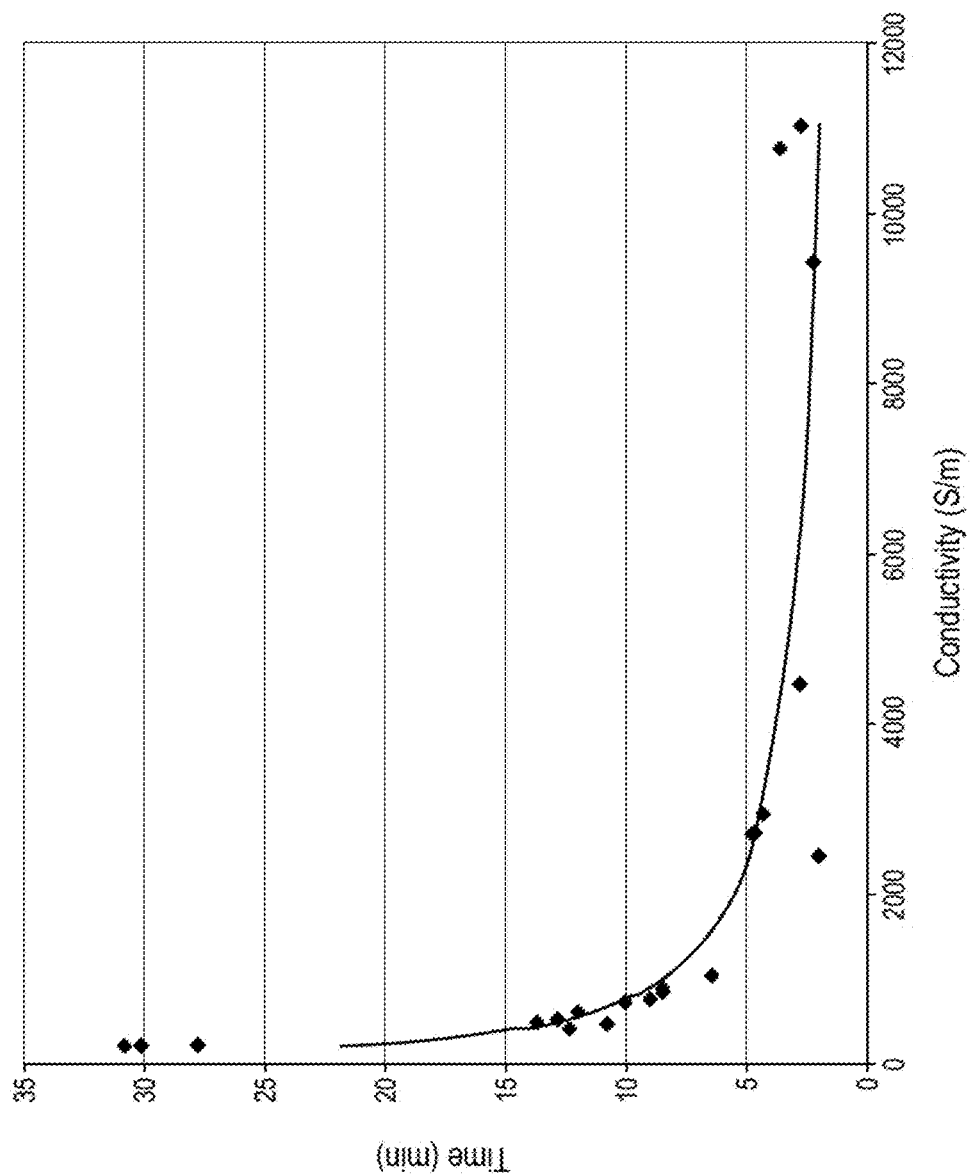
FIG. 8 is a graph showing how the time to form a 0.050 inch cut into the PDC table generally exponentially increases with decreasing electrical conductivity of the PCD table.

FIG. 8 charts data showing the effect of electrical conductivity on the time (minutes) required to EDM cut a 0.05 inch deep cut (e.g., similar to that shown in FIG. 7A). It is readily apparent from the charted data that as electrical conductivity decreases, the time required to form the EDM cut increases generally exponentially. The slope of the curve shows a relatively gradual increase in time required to form the cut at electrical conductivity values down to about 2000 S/m. Below about 2000 S/m, the time required to form the EDM cut increases significantly. For example, the 0.05 inch cut may be formed in less than about 5 minutes for electrical conductivity values greater than about 2000 S/m. At electrical conductivity values lower than about 2000 S/m the time to form the EDM cut is significantly greater. At about 1000 S/m the time required to form the EDM cut may be between about 5 minutes and about 10 minutes. At about 500 S/m the time required to form the EDM cut may be between about 10 minutes and about 15 minutes. At about 200 S/m, the time required to form the EDM cut may drastically increase to about 30 minutes. As seen in FIG. 8, in an embodiment, electrical conductivity for some PCD elements may be as high as about 10,000 S/m or even about 12,000 S/m.

As a practical matter, in an embodiment, the threshold value above which EDM of the screened PCD element occurs may be about 2000 S/m. At such a threshold, EDM can be achieved relatively quickly (e.g., within about 5 minutes or less for any of the cuts shown in FIG. 7A). Threshold values can be set at other electrical conductivity values (e.g., about 1000 S/m, about 500 S/m, about 200 S/m, about 200 S/m to about 2000 S/m, about 500 S/m to about 1500 S/m, or about 750 S/m to about 1000 S/m), depending on the nature of the particular EDM to be performed and other factors. Once the electrical conductivity of the PCD element is determined (or a characteristic that can be correlated to electrical conductivity is determined), the PCD element is sent down-line for EDM if the determined correlated characteristic correlates to an electrical conductivity above the applied threshold value. If the value of the determined correlated characteristic correlates to an electrical conductivity that is below the applied threshold value, then the PCD element is not suitable for EDM, but may be recycled, discarded as waste, or may be cut by another technique that does not rely on the same degree of electrical conductivity (e.g., laser cutting or grinding).

V. Embodiments of Products Including a PDC

The PDCs formed according to the various embodiments disclosed herein may be used as PDC cutting elements on a rotary drill bit, within thrust-bearing assemblies, radial bearing assemblies, and other applications. For example, in a method according to an embodiment of the invention, one or more PDCs that were screened and EDM according to any of the disclosed methods may be attached to a bit body of a rotary drill bit, brazed or otherwise mounted onto a support ring of a bearing assembly, or otherwise incorporated into a desired product.

Figure 9:
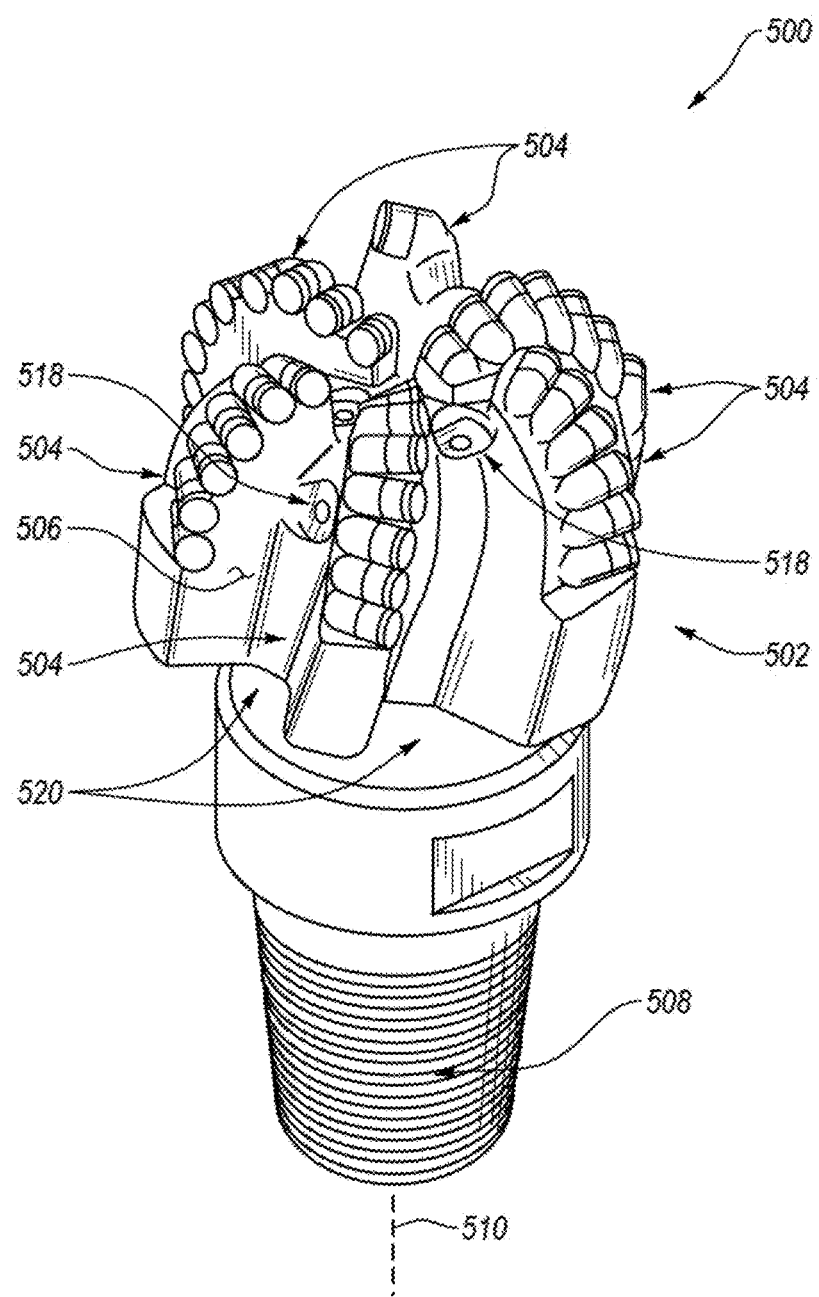
FIG. 9 is an isometric view of an embodiment of a rotary drill bit that may employ one or more of PDCs manufactured according to any of the disclosed embodiments.
Figure 10:
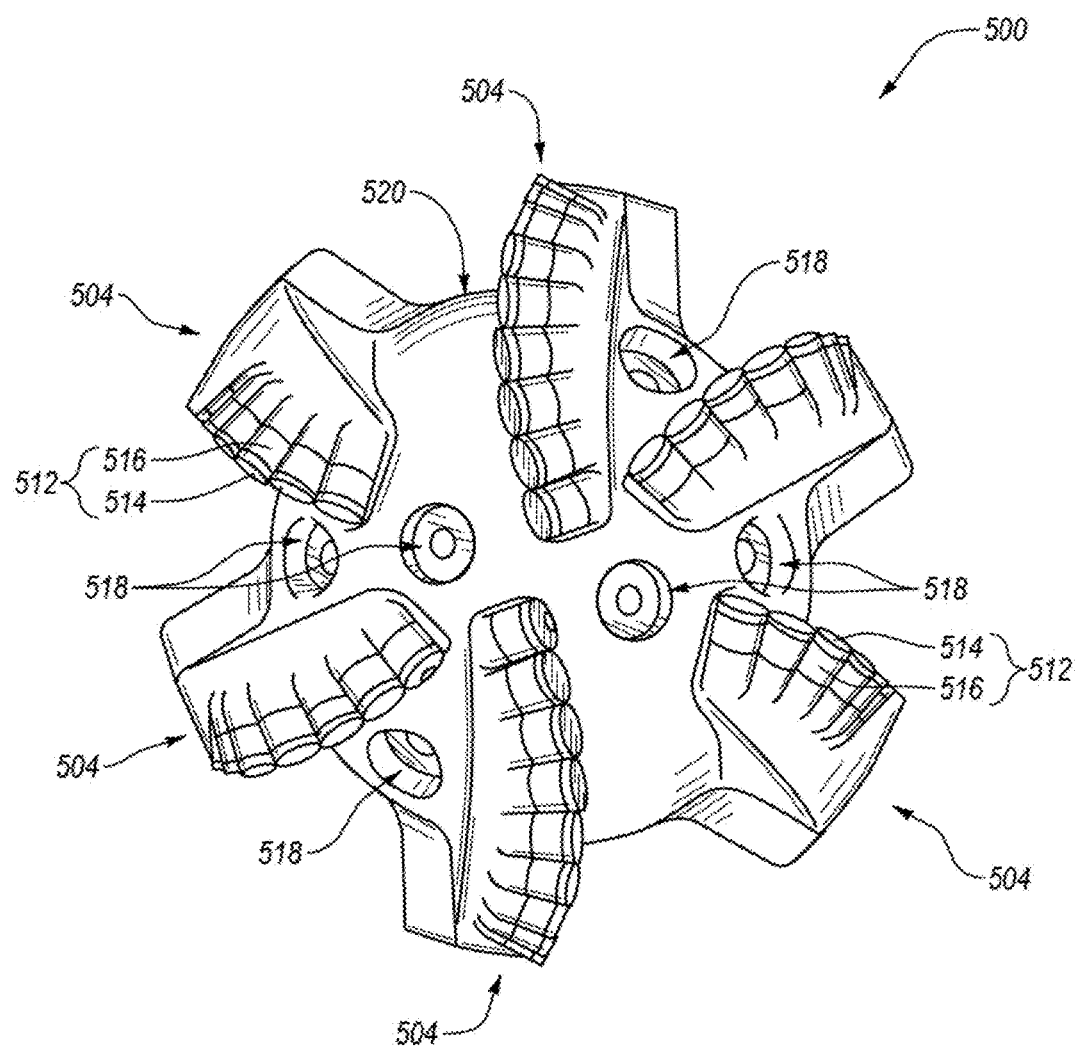
FIG. 10 is a top elevation view of the rotary drill bit shown in FIG. 9.

FIG. 9 is an isometric view and FIG. 10 is a top elevation view of an embodiment of a radial drill bit 500 that includes at least one PDC configured and/or fabricated according to any of the disclosed PDC embodiments. The rotary drill bit 500 comprises a bit body 502 that includes radially and longitudinally extending blades 504 having leading faces 506, and a threaded pin connection 508 for connecting the bit body 502 to a drilling string. The bit body 502 defines a leading end structure for drilling into a subterranean formation by rotation about a longitudinal axis 510 and application of weight-on-bit. At least one PDC, configured according to any of the previously described PDC embodiments, may be affixed to the bit body 502. With reference to FIG. 10, each of a plurality of PDCs 512 is secured to the blades 504 of the bit body 502 (FIG. 9). For example, each PDC 512 may include a PCD table 514 bonded to a substrate 516. More generally, the PDCs 512 may comprise any PDC disclosed herein, without limitation.

In addition, if desired, in some embodiments, a number of the PDCs 512 may not have been screened for EDM as described herein. Also, circumferentially adjacent blades 504 define so-called junk slots 520 therebetween. Additionally, the rotary drill bit 500 includes a plurality of nozzle cavities 518 for communicating drilling fluid from the interior of the rotary drill bit 500 to the PDCs 512.

FIGS. 9 and 10 merely depict one embodiment of a rotary drill bit that employs at least one PDC screened and EDM processed in accordance with the disclosed embodiments, without limitation. The rotary drill bit 500 is used to represent any number of earth-boring tools or drilling tools, including, for example, core bits, roller-cone bits, fixed-cutter bits, eccentric bits, bi-center bits, reamers, reamer wings, or any other downhole tool including superabrasive compacts, without limitation.

The PDCs screened and fabricated according to methods disclosed herein may also be utilized in applications other than cutting technology. For example, the disclosed PDC embodiments may be used in bearings or other articles of manufacture including at least one PCD table or compact.

Figure 11:
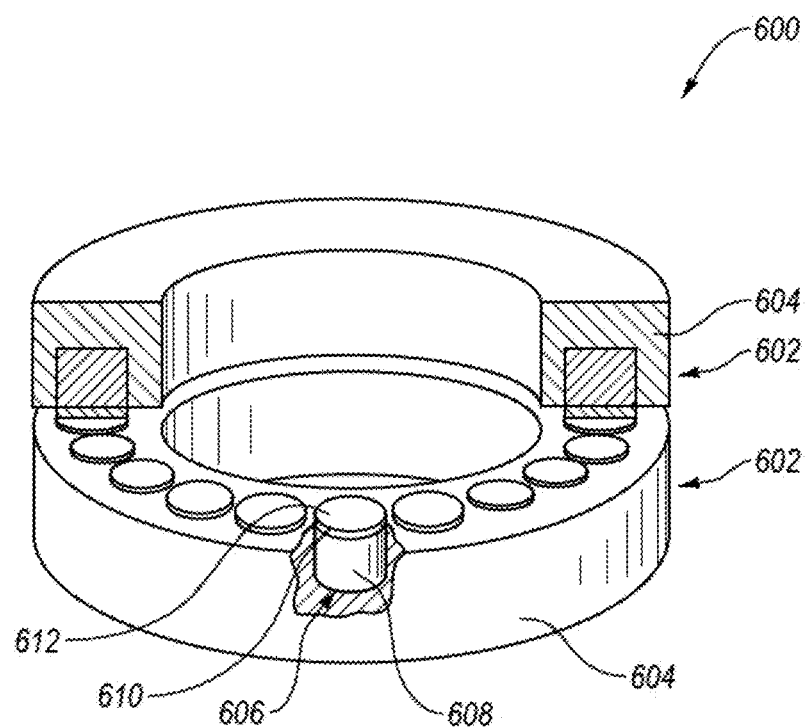
FIG. 11 is an isometric cut-away view of an embodiment of a thrust-bearing apparatus that may employ one or more PDCs manufactured according to any of the disclosed embodiments.

FIG. 11 is an isometric cut-away view of an embodiment of a thrust-bearing apparatus 600, which may utilize any of the disclosed PDC embodiments as bearing elements. The thrust-bearing apparatus 600 includes respective thrust-bearing assemblies 602. Each thrust-bearing assembly 602 includes an annular support ring 604 that may be fabricated from a material, such as carbon steel, stainless steel, or another suitable material. Each support ring 604 includes a plurality of recesses (not labeled) that receives a corresponding bearing element 606. Each bearing element 606 may be mounted to a corresponding support ring 604 within a corresponding recess by brazing, press-fitting, using fasteners, or another suitable mounting technique. One or more, or all of bearing elements 606 may be screened and EDM according to any of the disclosed methods prior to and/or after mounting to a corresponding support ring 604. For example, each bearing element 606 may include a substrate 608 and a PCD table 610, with the PCD table 610 including a bearing surface 612.

In use, the bearing surfaces 612 of one of the thrust-bearing assemblies 602 bears against the opposing bearing surfaces 612 of the other one of the bearing assemblies 602. For example, one of the thrust-bearing assemblies 602 may be operably coupled to a shaft to rotate therewith and may be termed a "rotor." The other one of the thrust-bearing assemblies 602 may be held stationary and may be termed a "stator."

Figure 12:
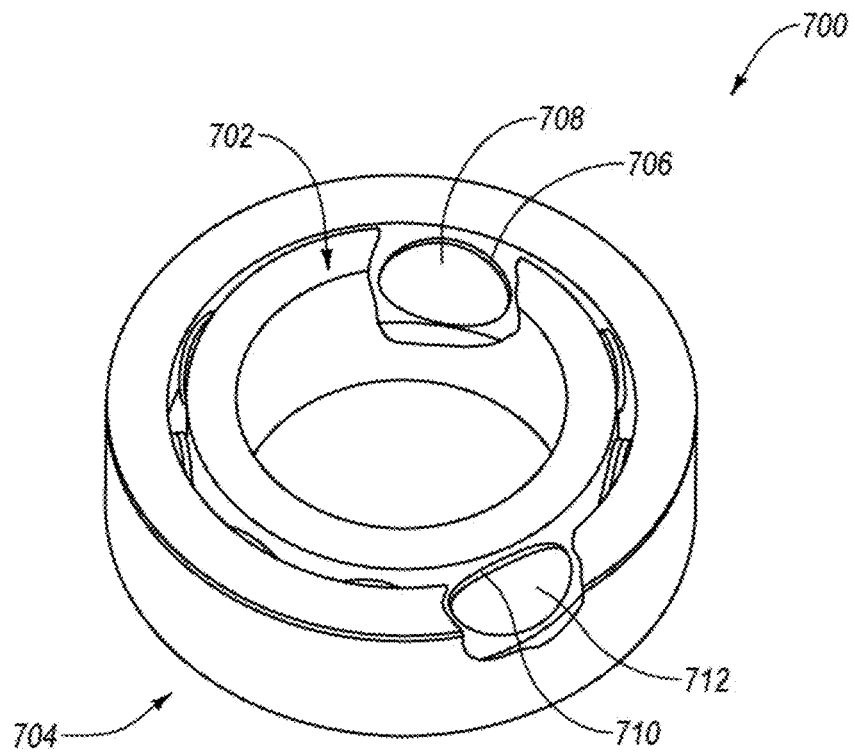
FIG. 12 is an isometric cut-away view of an embodiment of a radial bearing apparatus that may employ one or more PDCs manufactured according to any of the disclosed embodiments.

FIG. 12 is an isometric cut-away view of an embodiment of a radial bearing apparatus 700, which may employ PDCs that have been screened and EDM cut according to any of the disclosed methods. The radial bearing apparatus 700 includes an inner race 702 positioned generally within an outer race 704. The outer race 704 includes a plurality of bearing elements 706 mounted thereto that have respective bearing surfaces 708. For such a radial bearing, the bearing surface 708 of elements 706 mounted to outer race 704 may be concavely curved (see FIG. 7D). The inner race 702 also includes a plurality of bearing elements 710 affixed thereto that have respective bearing surfaces 712. For such a radial bearing, the bearing surface 712 of elements 710 mounted to inner race 702 may be convexly curved (see FIG. 7C) to mate with the concave curvature of bearing surface 708. The inner race 702 is positioned generally within the outer race 704 and, thus, the inner race 702 and outer race 704 may be configured so that the bearing surfaces 708 and 712 may at least partially contact one another and move relative to each other as the inner race 702 and outer race 704 rotate relative to each other during use. One or more, or all of the bearing elements 706 and 710 may be screened and EDM according to any of the methods disclosed herein. The bearing elements 706 and 710 may be brazed onto respective races 704 and 702. According to an embodiment, brazing of the bearing elements only occurs after suitability for EDM processing has been determined. This prevents a PCD element that is not suitable for EDM from being brazed in place, which may lead to the radial bearing having to be scrapped. After the bearing elements 706, 708 are brazed to corresponding inner and outer races 702, 704, the curvature of the bearing surfaces 708, 712 may be formed and/or adjusted via EDM.

The radial-bearing apparatus 700 may be employed in a variety of mechanical applications. For example, so-called "roller cone" rotary drill bits may benefit from a radial-bearing apparatus disclosed herein. More specifically, the inner race 702 may be mounted to a spindle of a roller cone and the outer race 704 may be mounted to an inner bore formed within a cone and that such an outer race 704 and inner race 702 may be assembled to form a radial-bearing apparatus.

Figure 13:
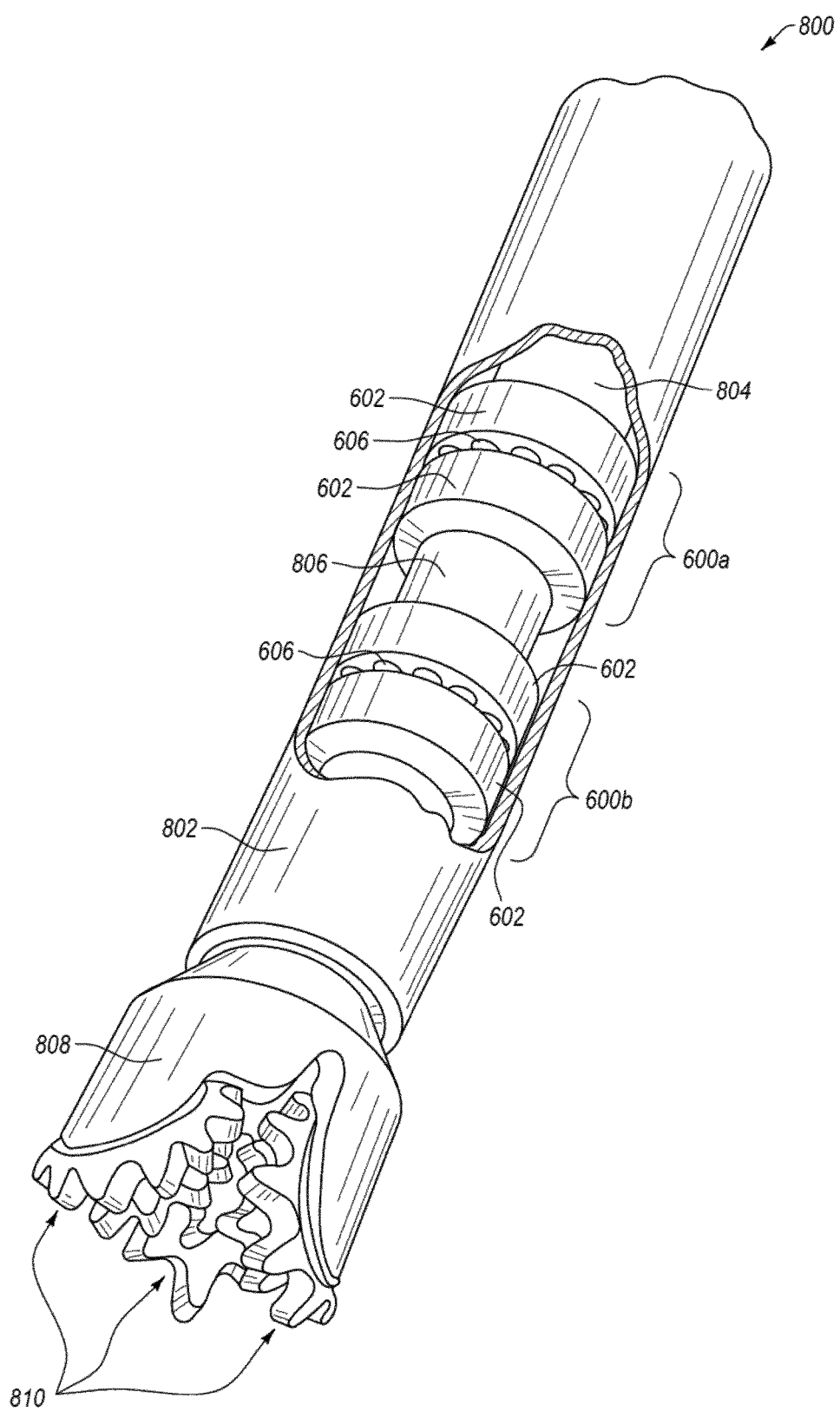
FIG. 13 is a schematic isometric cut-away view of an embodiment of a subterranean drilling system including the thrust-bearing apparatus shown in FIG. 11.

Referring to FIG. 13, the thrust-bearing apparatus 600 and/or radial bearing apparatus 700 may be incorporated in a subterranean drilling system. FIG. 13 is a schematic isometric cut-away view of a subterranean drilling system 800 that includes at least one of the thrust-bearing apparatuses 600 shown in FIG. 11 according to another embodiment. The subterranean drilling system 800 includes a housing 802 enclosing a downhole drilling motor 804 (i.e., a motor, turbine, or any other device capable of rotating an output shaft) that is operably connected to an output shaft 806. A first thrust-bearing apparatus 600a (FIG. 11) is operably coupled to the downhole drilling motor 804. A second thrust-bearing apparatus 600b (FIG. 11) is operably coupled to the output shaft 806. A rotary drill bit 808 configured to engage a subterranean formation and drill a borehole is connected to the output shaft 806. The rotary drill bit 808 is shown as a roller cone bit including a plurality of roller cones 810.

However, other embodiments may employ different types of rotary drill bits, such as a so-called "fixed cutter" drill bit shown in FIGS. 9-10. As the borehole is drilled, pipe sections may be connected to the subterranean drilling system 800 to form a drill string capable of progressively drilling the borehole to a greater depth within the earth.

A first one of the thrust-bearing assemblies 602 of the thrust-bearing apparatus 600a is configured as a stator that does not rotate and a second one of the thrust-bearing assemblies 602 of the thrust-bearing apparatus 600a is configured as a rotor that is attached to the output shaft 806 and rotates with the output shaft 806. The on-bottom thrust generated when the drill bit 808 engages the bottom of the borehole may be carried, at least in part, by the first thrust-bearing apparatus 600a. A first one of the thrust-bearing assemblies 602 of the second thrust-bearing apparatus 600b is configured as a stator that does not rotate and a second one of the thrust-bearing assemblies 602 of the thrust-bearing apparatus 600b is configured as a rotor that is attached to the output shaft 806 and rotates with the output shaft 806. Fluid flow through the power section of the downhole drilling motor 804 may cause what is commonly referred to as "off-bottom thrust," which may be carried, at least in part, by the second thrust-bearing apparatus 600b.

In operation, drilling fluid may be circulated through the downhole drilling motor 804 to generate torque and effect rotation of the output shaft 806 and the rotary drill bit 808 attached thereto so that a borehole may be drilled. A portion of the drilling fluid may also be used to lubricate opposing bearing surfaces of the bearing elements 606 of the thrust-bearing assemblies 602.

Thus, PDCs that are screened and subsequently EDM processed as disclosed herein may be used in any apparatus or structure in which at least one PDC is typically used. In an embodiment, a rotor and a stator, assembled to form a thrust-bearing apparatus, may each include one or more PDCs (e.g., PDC 200 of FIG. 2) configured according to any of the embodiments disclosed herein and may be operably assembled to a downhole drilling assembly. U.S. Pat. Nos. 4,410,054; 4,560,014; 5,364,192; 5,368,398; 5,480,233; 7,552,782; and 7,559,695, the disclosure of each of which is incorporated herein, in its entirety, by this reference, disclose subterranean drilling systems within which bearing apparatuses utilizing superabrasive compacts disclosed herein may be incorporated. The embodiments of PDCs disclosed herein may also form all or part of heat sinks, wire dies, bearing elements, cutting elements, cutting inserts (e.g., on a roller-cone-type drill bit), machining inserts, or any other article of manufacture as known in the art. Other examples of articles of manufacture that may use any of the PDCs disclosed herein are disclosed in U.S. Pat. Nos. 4,811,801; 4,268,276; 4,468,138; 4,738,322; 4,913,247; 5,016,718; 5,092,687; 5,120,327; 5,135,061; 5,154,245; 5,460,233; 5,544,713; and 6,793,681, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A method of fabricating a bearing assembly, the method comprising:
   providing a polycrystalline diamond ("PCD") element including a PCD volume;
   determining a plurality of electrical conductivities of the PCD volume; and
   brazing the PCD element to a bearing support ring upon determining that an average of the plurality of electrical conductivities is above a threshold value.

2. The method of claim 1, wherein the PCD volume is formed by placing a layer including of un-bonded diamond particles adjacent to a carbide substrate and subjecting the layer and the carbide substrate to a high-pressure/high-temperature process.

3. The method of claim 1, further comprising, after brazing the PCD element to the bearing support ring, electro-discharge machining the PCD element to define a bearing surface.

4. A method of fabricating a bearing assembly, the method comprising:
   providing a polycrystalline diamond ("PCD") element including a PCD volume;
   determining a plurality of electrical conductivities of the PCD volume including measuring an electrical resistance between a plurality of locations of the PCD volume with an electrical impedance tomography system; and
   brazing the PCD element to a bearing support ring upon determining that at least one of the plurality of electrical conductivities is above a threshold value.

5. The method of claim 1, wherein the threshold value is about 200 S/m.

6. The method of claim 1, wherein the threshold value is about 500 S/m.

7. The method of claim 1, wherein the threshold value is about 1000 S/m.

8. The method of claim 1, wherein the threshold value is about 2000 S/m.

9. The method of claim 1, wherein the plurality of electrical conductivities of the PCD volume is calculated by measuring a plurality of electrical resistances of the PCD volume and calculating the plurality of electrical conductivities from the measured plurality of electrical resistances.

10. The method of claim 1, wherein the PCD element includes a substrate and the PCD volume is bonded to the substrate.

11. A method of fabricating a bearing assembly, the method comprising:
    providing a polycrystalline diamond ("PCD") element including a PCD volume, the PCD volume exhibiting a coercivity of about 115 Oe or more and a metal-solvent catalyst content of less than about 7.5% by weight;
    determining a plurality of electrical conductivities of the PCD volume;
    brazing the PCD element to a bearing support ring upon determining that an average of the plurality of electrical conductivities of the PCD volume is above a threshold value; and
    after brazing the PCD element to the bearing support ring, electro-discharge machining the PCD element to define a bearing surface.

12. The method of claim 11, wherein the bearing surface is convexly curved or concavely curved.

13. A method of fabricating a bearing assembly, the method comprising:
    providing a polycrystalline diamond ("PCD") element including a PCD volume, the PCD volume exhibiting a coercivity of about 115 Oe or more and a metal-solvent catalyst content of less than about 7.5% by weight;
    determining a plurality of electrical conductivities of the PCD volume including measuring an electrical resistance between a plurality of locations of the PCD volume with an electrical impedance tomography system;
    brazing the PCD element to a bearing support ring upon determining that at least one of the plurality of electrical conductivities of the PCD volume is above a threshold value; and
    after brazing the PCD element to the bearing support ring, electro-discharge machining the PCD element to define a bearing surface.

14. The method of claim 11, wherein brazing the PCD element to a bearing support ring if at least one of the plurality of electrical conductivities is above a threshold value includes brazing the PCD element to the bearing support ring if an average of the plurality of electrical conductivities is above the threshold value.

15. The method of claim 11, wherein the coercivity is about 115 Oe to about 250 Oe and the PCD volume exhibits a specific magnetic saturation greater than zero $G \cdot cm^3/g$ to about 15 $G \cdot cm^3/g$.

16. The method of claim 15, wherein the coercivity is about 115 Oe to about 175 Oe and the specific magnetic saturation is about 5 $G \cdot cm^3/g$ to about 15 $G \cdot cm^3/g$.

17. The method of claim 11, wherein the threshold value is about 200 S/m.

18. The method of claim 11, wherein the threshold value is about 500 S/m.

19. The method of claim 11, wherein the threshold value is about 1000 S/m.

20. The method of claim 11, wherein the PCD element includes a substrate and the PCD volume is bonded to the substrate.

* * * * *